(12) United States Patent
Bencini et al.

(10) Patent No.: US 7,695,451 B2
(45) Date of Patent: Apr. 13, 2010

(54) STEERABLE DEVICE FOR INTRODUCING DIAGNOSTIC AND THERAPEUTIC APPARATUS INTO THE BODY

(75) Inventors: Robert F. Bencini, Sunnyvale, CA (US); Bernard J. Durman, Pleasanton, CA (US); Peter Franklin Campbell, San Jose, CA (US); Brandon Shuman, Kirkland, WA (US); Russell B. Thompson, Los Altos, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 263 days.

(21) Appl. No.: 11/304,078

(22) Filed: Dec. 15, 2005

(65) Prior Publication Data

US 2006/0184107 A1 Aug. 17, 2006

Related U.S. Application Data

(63) Continuation of application No. 10/354,345, filed on Jan. 29, 2003, now Pat. No. 6,991,616, which is a continuation of application No. 09/165,652, filed on Oct. 2, 1998, now Pat. No. 6,544,215.

(51) Int. Cl.
*A61M 31/00* (2006.01)
*A61M 25/00* (2006.01)
*A61M 37/00* (2006.01)

(52) U.S. Cl. .................... 604/95.04; 604/524

(58) Field of Classification Search .......... 604/95.01, 604/95.04, 523–526, 528, 529
See application file for complete search history.

(56) References Cited

U.S. PATENT DOCUMENTS

| | | | | | |
|---|---|---|---|---|---|
| 7,356 | A | * | 5/1850 | Atwood | 126/77 |
| 62,961 | A | * | 3/1867 | Keyser | 126/58 |
| 71,129 | A | * | 11/1867 | Bush et al. | 126/83 |
| 76,315 | A | * | 4/1868 | Evard | 126/1 AE |
| 111,129 | A | * | 1/1871 | Macaulay | 112/234 |
| 111,729 | A | * | 2/1871 | Croll | 116/170 |
| 114,614 | A | * | 5/1871 | Smith | 126/98 |
| 117,129 | A | * | 7/1871 | Walker | 454/36 |
| 123,142 | A | * | 1/1872 | Beckwith | 126/58 |
| 127,535 | A | * | 6/1872 | Whittingham | 126/98 |
| 135,621 | A | * | 2/1873 | Beckwith | 126/98 |

(Continued)

FOREIGN PATENT DOCUMENTS

DE        43 36 040 A1    4/1995

(Continued)

OTHER PUBLICATIONS

English language translation of the text of DE 43 36 040 A1.

(Continued)

*Primary Examiner*—Kevin C Sirmons
*Assistant Examiner*—Michael J Anderson
(74) *Attorney, Agent, or Firm*—Henricks, Slavin & Holmes LLP

(57) ABSTRACT

An apparatus including an elongate body having a lumen extending therethrough and a steering wire, having a distal portion defining a non-circular cross-section, associated with the distal portion of the elongate body.

19 Claims, 10 Drawing Sheets

U.S. PATENT DOCUMENTS

| | | | |
|---|---|---|---|
| 135,631 A * | 2/1873 | Corser | 241/300.1 |
| 164,166 A * | 6/1875 | Gordon | 426/624 |
| 171,129 A * | 12/1875 | Hermance | 254/25 |
| 3,470,876 A | 10/1969 | Barchilon | |
| 4,586,923 A | 5/1986 | Gould et al. | |
| 4,664,113 A | 5/1987 | Frisbie et al. | |
| 4,719,924 A | 1/1988 | Crittenden et al. | |
| 4,723,936 A | 2/1988 | Buchbinder et al. | |
| 4,757,827 A | 7/1988 | Buchbinder et al. | |
| 4,898,577 A | 2/1990 | Badger | |
| 4,906,230 A | 3/1990 | Maloney et al. | |
| 4,920,980 A | 5/1990 | Jackowski | |
| 4,934,340 A | 6/1990 | Ebling et al. | |
| 4,960,411 A | 10/1990 | Buchbinder | |
| 5,030,204 A | 7/1991 | Badger et al. | |
| 5,114,403 A | 5/1992 | Clarke et al. | |
| 5,114,414 A | 5/1992 | Buchbinder | |
| 5,125,896 A | 6/1992 | Hojeibane | |
| 5,199,950 A | 4/1993 | Schmitt et al. | |
| 5,231,989 A | 8/1993 | Middleman et al. | |
| 5,255,668 A | 10/1993 | Umeda | |
| 5,318,525 A | 6/1994 | West | |
| 5,336,182 A * | 8/1994 | Lundquist et al. | 604/528 |
| 5,342,299 A | 8/1994 | Snoke et al. | |
| 5,345,945 A * | 9/1994 | Hodgson et al. | 600/585 |
| 5,363,861 A | 11/1994 | Edwards | |
| 5,368,564 A | 11/1994 | Savage | |
| 5,381,782 A | 1/1995 | DeLaRama et al. | |
| 5,391,146 A | 2/1995 | That et al. | |
| 5,395,327 A * | 3/1995 | Lundquist et al. | 604/95 |
| 5,409,483 A | 4/1995 | Campbell et al. | |
| 5,419,340 A | 5/1995 | Stevens | |
| 5,419,764 A | 5/1995 | Roll | |
| 5,431,168 A * | 7/1995 | Webster, Jr. | 600/435 |
| 5,472,017 A * | 12/1995 | Kovalcheck | 138/103 |
| 5,477,856 A | 12/1995 | Lundquist | |
| 5,484,407 A | 1/1996 | Osypka | |
| 5,507,725 A | 4/1996 | Savage et al. | |
| 5,531,686 A * | 7/1996 | Lundquist et al. | 604/95.04 |
| 5,531,687 A | 7/1996 | Snoke et al. | |
| 5,603,697 A | 2/1997 | Grundy | |
| 5,611,777 A | 3/1997 | Bowden | |
| 5,636,634 A | 6/1997 | Kordis | |
| 5,676,653 A | 10/1997 | Taylor et al. | |
| 5,690,642 A | 11/1997 | Osborne et al. | |
| 5,702,433 A | 12/1997 | Taylor et al. | |
| 5,820,591 A | 10/1998 | Thompson et al. | |
| 5,827,278 A * | 10/1998 | Webster | 606/41 |
| 5,843,020 A | 12/1998 | Tu et al. | |
| 5,855,560 A | 1/1999 | Idaomi et al. | |
| 5,857,997 A | 1/1999 | Cimino | |
| 5,876,340 A | 3/1999 | Tu et al. | |
| 5,876,373 A | 3/1999 | Giba et al. | |
| 5,882,333 A | 3/1999 | Schaer et al. | |
| 5,897,529 A | 4/1999 | Ponzi | |
| 5,908,405 A | 6/1999 | Imran et al. | |
| 5,916,147 A | 6/1999 | Boury | |
| 5,935,102 A | 8/1999 | Bowden et al. | |
| 5,938,616 A | 8/1999 | Eaton et al. | |
| 6,030,360 A | 2/2000 | Biggs | |
| 6,059,739 A | 5/2000 | Baumann | |
| 6,066,125 A | 5/2000 | Webster, Jr. | |
| 6,083,170 A | 7/2000 | Ben-Haim | |
| 6,146,355 A | 11/2000 | Biggs | |
| 6,213,974 B1 | 4/2001 | Smith et al. | |
| 6,450,948 B1 | 9/2002 | Matsuura et al. | |
| 6,491,681 B1 | 12/2002 | Kunis et al. | |
| 6,544,215 B1 | 4/2003 | Bencini et al. | |
| 6,991,616 B2 | 1/2006 | Bencini et al. | |
| 2008/0188800 A1 | 8/2008 | Bencini et al. | |
| 2008/0188801 A1 | 8/2008 | Bencini et al. | |

FOREIGN PATENT DOCUMENTS

| | | |
|---|---|---|
| EP | 0489937 B1 | 6/1995 |
| EP | 0689851 A | 1/1996 |
| EP | 0815895 A | 1/1998 |
| WO | WO-97/27895 A | 8/1997 |
| WO | WO-99/33509 A | 7/1999 |
| WO | WO-99/62585 A | 12/1999 |
| WO | WO-00/06242 A | 2/2000 |
| WO | WO-00/15286 A | 3/2000 |
| WO | WO-00/18323 A | 4/2000 |
| WO | WO-00/22981 A | 4/2000 |

OTHER PUBLICATIONS

Office Action dated Jun. 22, 2009 in U.S. Appl. No. 11/923,536.
U.S. Appl. No. 09/548,465 as filed.
Claims in U.S. Appl. No. 09/548,465 as of Aug. 4, 2009.
Office Action dated Apr. 10, 2002 in U.S. Appl. No. 09/548,465.
Office Action dated Sep. 25, 2002 in U.S. Appl. No. 09/548,465.
Office Action dated Mar. 6, 2003 in U.S. Appl. No. 09/548,465.
Office Action dated Aug. 29, 2003 in U.S. Appl. No. 09/548,465.
Office Action dated Nov. 25, 2003 in U.S. Appl. No. 09/548,465.
Office Action dated Dec. 17, 2003 in U.S. Appl. No. 09/548,465.
Office Action dated Jul. 20, 2004 in U.S. Appl. No. 09/548,465.
Office Action dated Jan. 12, 2005 in U.S. Appl. No. 09/548,465.
Office Action dated Aug. 5, 2005 in U.S. Appl. No. 09/548,465.
Office Action dated Feb. 13, 2006 in U.S. Appl. No. 09/548,465.
Office Action dated Jun. 29, 2006 in U.S. Appl. No. 09/548,465.
Office Action dated Oct. 6, 2006 in U.S. Appl. No. 09/548,465.
Office Action dated Apr. 20, 2007 in U.S. Appl. No. 09/548,465.
Office Action dated Oct. 2, 2007 in U.S. Appl. No. 09/548,465.
Office Action dated Apr. 14, 2008 in U.S. Appl. No. 09/548,465.
Office Action dated Nov. 14, 2008 in U.S. Appl. No. 09/548,465.
Office Action dated Jul. 21, 2009 in U.S. Appl. No. 09/548,465.

* cited by examiner

STEERABLE DEVICE FOR INTRODUCING DIAGNOSTIC AND THERAPEUTIC APPARATUS INTO THE BODY

CROSS-REFERENCE TO RELATED APPLICATIONS

This application is a continuation of application Ser. No. 10/354,345, filed Jan. 29, 2003, now U.S. Pat. No. 6,991,616, which is a continuation of application Ser. No. 09/165,652, filed Oct. 2, 1998, now U.S. Pat. No. 6,544,215.

BACKGROUND OF THE INVENTIONS

1. Field of Inventions

The present invention relates generally to devices that are used to introduce diagnostic and therapeutic apparatus into the body.

2. Description of the Related Art

There are many instances where physicians must introduce diagnostic and therapeutic apparatus, such as diagnostic and therapeutic electrodes, ultrasound transducers, biopsy devices and other surgical tools, into the body. The diagnostic and therapeutic apparatus are often carried by catheters, which allow physicians to gain access to the body in a minimally invasive manner by way of bodily lumens. In cardiac treatment, for example, a catheter is advanced through a main vein or artery into the region of the heart that is to be treated.

One method of introducing diagnostic and therapeutic apparatus into the body is to introduce a tubular member (typically a "sheath") into the vicinity of the targeted region. A diagnostic or therapeutic apparatus is then passed through the tubular member to the targeted region. If necessary, the diagnostic or therapeutic apparatus may be removed after its function is performed, but the tubular member left in place, so that other apparatus may be advanced to the targeted region to complete the diagnostic and/or therapeutic procedure.

Precise placement of the diagnostic or therapeutic apparatus is very important, especially in those procedures concerning the heart. To that end, some conventional sheaths are guided to the targeted region with a steerable catheter that is located within the sheath lumen. Once the sheath reaches the targeted region, the steerable catheter is removed from the sheath and a catheter carrying the diagnostic or therapeutic apparatus is advanced through the lumen. This type of sheath lacks any onboard steering mechanism. As a result, redeployment of the distal portion of sheath, even to a region in close proximity to the initially targeted region, requires the withdrawal of the diagnostic or therapeutic apparatus and the reintroduction of the steering catheter.

Other conventional sheaths include a steering mechanism that allows the physician to deflect the distal portion of the sheath. The steering mechanism consists primarily of one or more steering wires. One end of each steering wire is secured to the distal end of the sheath, while the other end is secured to a steering control device, such as the rotating cam and steering control knob arrangement commonly found in steerable catheters. Rotation of the control knob causes one of the wires to impart a pulling force on the distal portion of the sheath, thereby causing the distal portion to deflect. To promote steerability, the distal portion of the sheath (which is relatively short) is typically formed from relatively soft, flexible material. Conversely, the proximal portion (which is relatively long) is formed from relatively hard, less flexible material that provides better torque transmission properties.

The inventors herein have determined that there are a number of shortcomings associated with conventional steerable apparatus, such as steerable sheaths, that are used to introduce diagnostic and therapeutic apparatus into the body. For example, it is desirable to provide a sheath or other tubular member having a small outer diameter (OD) in order to limit the size of the entry hole that must be made in the patient's vein or artery and to compensate for the effects of arteriosclerosis. Because the diameter of the lumen, or inner diameter (ID), tends to be a function of the size of the diagnostic and therapeutic apparatus to be introduced into the body, the primary method of reducing the OD is reducing the wall thickness of the tubular member.

Heretofore, efforts to reduce wall thickness have been hampered by the fact that the wall strength of the tubular member distal portion must be sufficient to prevent the steering wire from tearing through the distal portion during deflection. Proposed solutions to the strength problem included the use of harder materials and/or the addition of mechanical devices, such as coils, to the distal portion of the tubular member. The inventors herein have determined that such solutions are less than optimal because they limit the flexibility and, therefore, the steerability of the distal portion of the sheath or other tubular member.

SUMMARY OF THE INVENTIONS

Accordingly, the general object of the present inventions is to provide a apparatus that avoids, for practical purposes, the aforementioned problems. In particular, one object of the present inventions is to provide a steerable apparatus for introducing diagnostic and therapeutic apparatus into the body, such as a steerable sheath, having a thinner wall than conventional apparatus without sacrificing steerability.

In order to accomplish some of these and other objectives, an apparatus in accordance with one embodiment of a present invention includes an elongate body having a lumen extending therethrough and a steering wire, having a distal portion defining a non-circular cross-section, associated with the distal portion of the elongate body. In one preferred implementation, the elongate body is a sheath and the distal portion of the steering wire is substantially flat.

The present apparatus provides a number of advantages over conventional steerable apparatus for introducing diagnostic and therapeutic apparatus into the body. For example, the non-circular steering wire distal portion distributes the forces generated during deflection over a greater surface area than a steering wire having a circular cross-section. The redistribution of forces over a greater area reduces the amount strength required to prevent the steering wire from tearing through the distal portion of the tubular members, sheaths or other elongate bodies during deflection. As a result, the present elongate body may be made thinner than the tubular members, sheaths or other elongate bodies in conventional steerable apparatus formed from the same material.

Use of the present non-circular steering wire also prevents out of plane bending. The non-circular portion of the steering wire also provides a larger surface area for attaching the steering wire to the distal portion of the elongate body or an element within the elongate body, thereby making manufacturing easier and, due to the larger bonding area, decreasing the likelihood that the steering wire and elongate body with become disconnected.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 6b is a top view of the elongate body distal portion illustrated in FIG. 6a.

FIG. 7b is a top view of the elongate body distal portion illustrated in FIG. 7a.

DETAILED DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:
I. Overview
II. Elongate Body Distal Portion
III. Elongate Body Proximal Portion
IV. Handle The section titles and overall organization of the present detailed description are for the purpose of convenience only and are not intended to limit the present inventions.

I. Overview

The present inventions may be used within body lumens, chambers or cavities for diagnostic or therapeutic purposes in those instance where access to interior bodily regions is obtained through, for example, the vascular system or alimentary canal and without complex invasive surgical procedures. For example, the inventions herein have application in the diagnosis and treatment of conditions within the heart. The inventions herein also have application in the diagnosis or treatment of ailments of the gastrointestinal tract, prostrate, brain, gall bladder, uterus, and other regions of the body.

Figure 1:
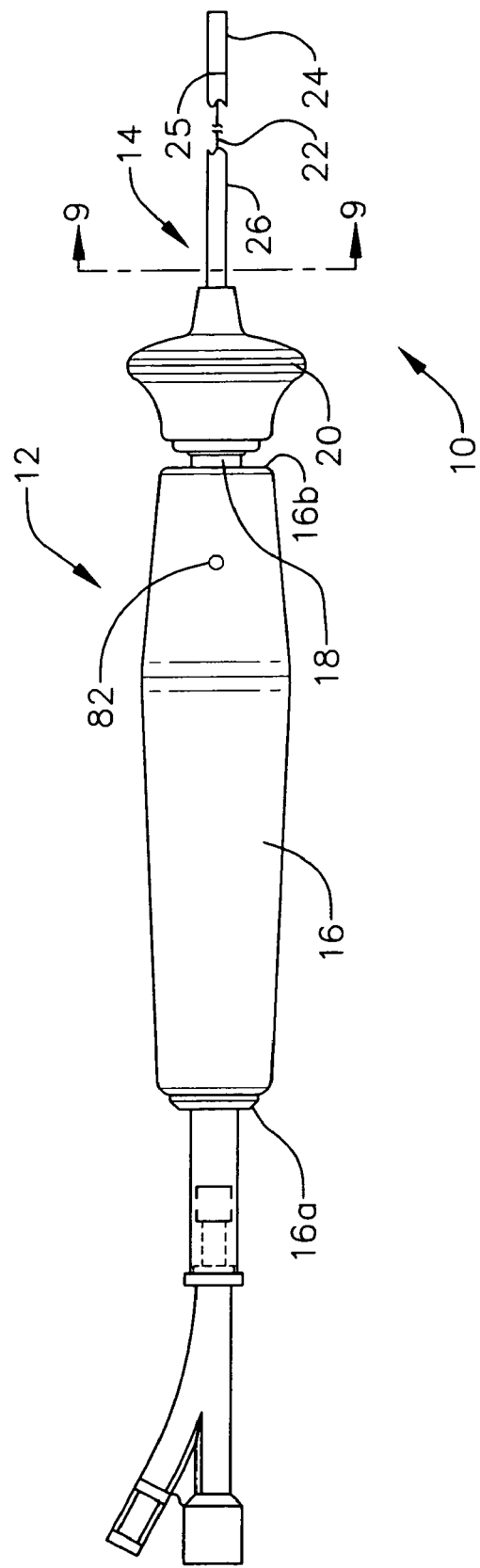
FIG. 1 is a plan view of a steerable apparatus in accordance with a preferred embodiment of a present invention.

As illustrated for example in FIG. 1, a preferred implementation of a present invention is a steerable device 10 having a handle 12 and an elongate, hollow body 14. In the preferred implementation, the elongate body 14 is a sheath having a lumen through which a catheter having diagnostic and/or therapeutic element(s) may be advanced.

The exemplary handle 12 consists partially of a handle body 16 (which has a proximal longitudinal end 16a and a distal longitudinal end 16b) and a piston 18. The piston 18, which is slidably mounted in a longitudinally extending aperture in the handle body 16, includes a thumb rest 20. The handle body 16, piston 18 and thumb rest 20 are preferably formed from machined or molded plastic. Other features of the exemplary handle 12 are discussed below in Section IV. In the exemplary embodiment, one end of a steering wire 22 is secured to the distal portion 24 of the elongate body 14. The steering wire 22 passes through the proximal portion 26 of the elongate body 14 to the handle body 16, where the other end is secured. As discussed in Section III below, the elongate body distal portion 24 and proximal portion 26 are joined to one another at a joint 25.

In the illustrated embodiment, the elongate body is secured to, and travels with, the piston 18. As such, when the exemplary piston 18 is moved distally from the position shown in FIG. 1, the steering wire 22 exerts a pulling force on the distal portion 24 of the elongate body 14, thereby causing the distal portion of the elongate body to deflect into a curved orientation.

Other types of steering apparatus may be used in place of the exemplary piston-based configuration. For example, a handle may be provided that includes a rotating cam, to which the steering wire is connected, and a steering lever connected to the rotating cam. Manipulation of the steering lever causes the steering wire to deflect the distal portion of the elongate body. This type of steering apparatus is disclosed in U.S. Pat. No. 5,636,634.

Figure 2:
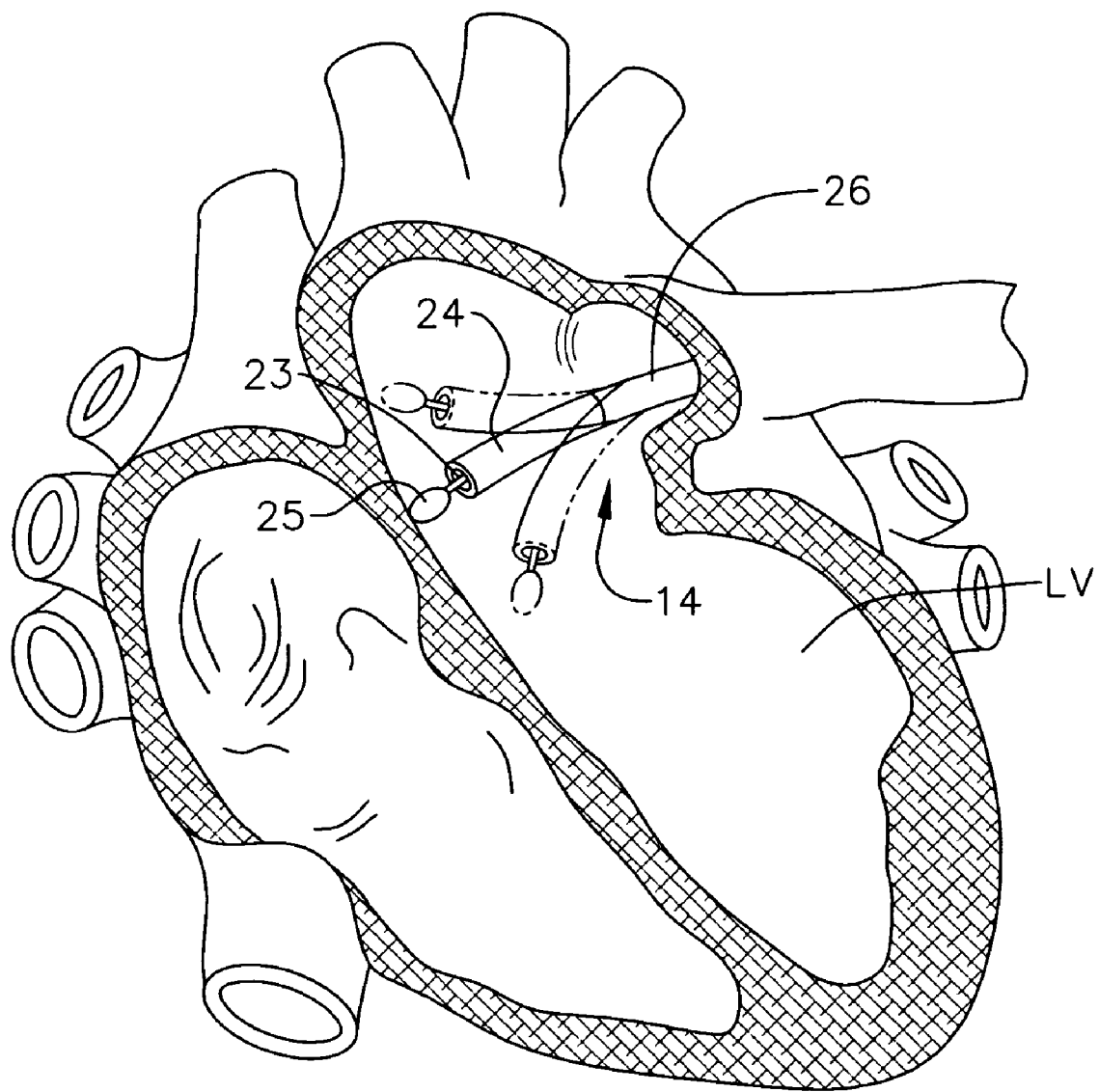
FIG. 2 is a partial section view showing a steerable apparatus in accordance with a preferred embodiment of a present invention, in combination with a catheter carrying a diagnostic or therapeutic element, deployed within the heart.

One exemplary use of the present steerable device is illustrated in FIG. 2. Here, the distal portion 24 of the elongate body 14 has been inserted into the heart and steered into the vicinity of targeted tissue within the left ventricle LV. It should be noted that the heart shown in FIG. 2 is not exactly anatomically correct, and is shown in diagrammatic form to demonstrate the features of the exemplary device. A catheter 23 is extending from the distal portion 24 so that an element 25 (such as a diagnostic and/or therapeutic element) may be positioned adjacent myocardial tissue.

II. Elongate Body Distal Portion

Figure 3:
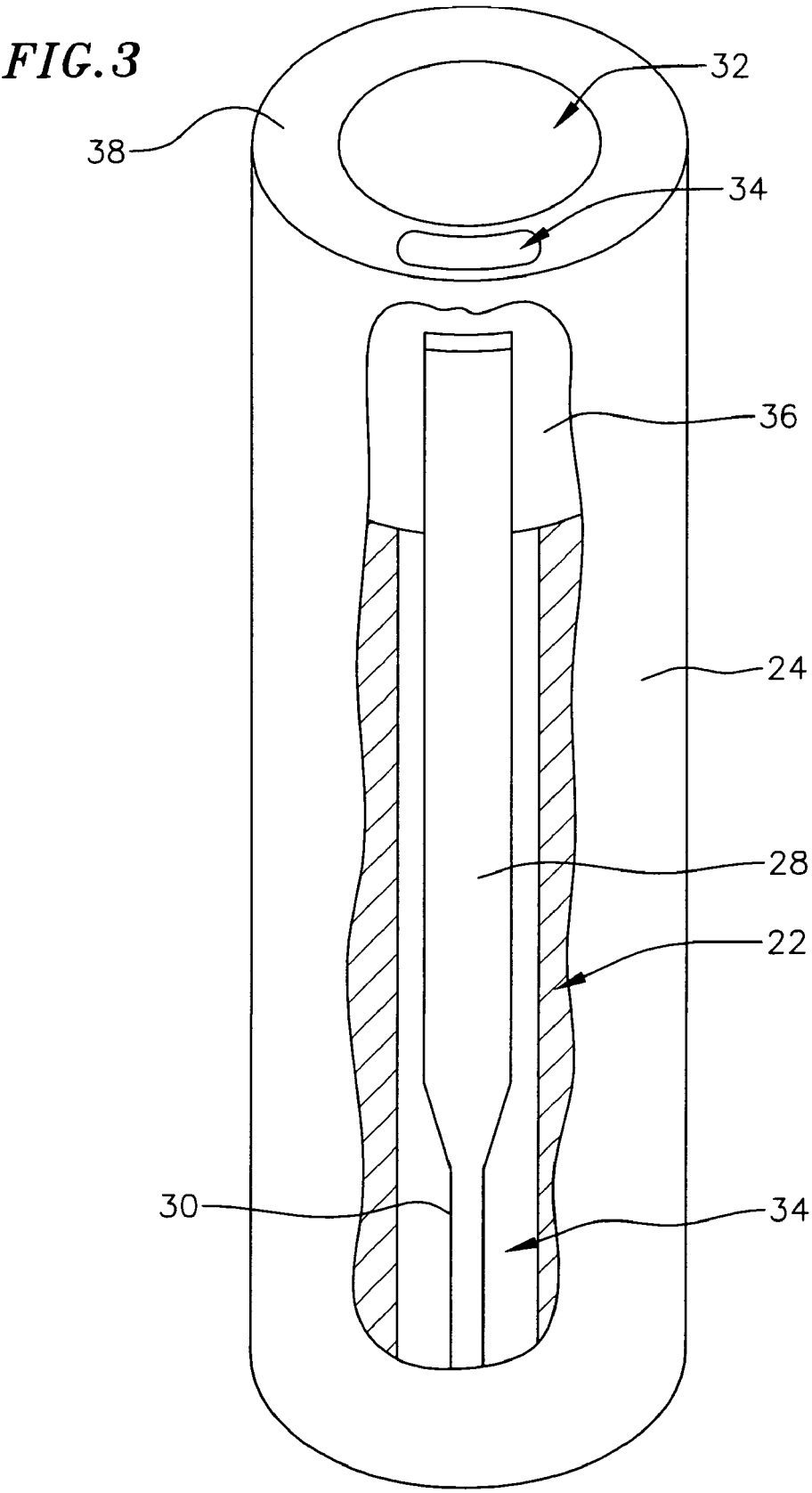
FIG. 3 is a perspective, partial section view of an elongate body distal portion in accordance with a preferred embodiment of a present invention.

In accordance with a preferred embodiment of a present invention, and as illustrated for example in FIG. 3, the portion of the steering wire 22 that is secured to the distal portion 24 of the elongate body 14 has a non-circular cross-section. Although other shapes may be employed, the distal portion 28 of the exemplary steering wire 22 (also referred to as the "non-circular portion") is substantially flat and preferably free of sharp edges that could damage the distal portion 24 of the elongate body 14. A substantially flat steering wire distal portion 28 having a width to thickness ratio between about 1.5 to 1 and about 10 to 1 is preferred. The remainder of the steering wire (referred to herein as the proximal portion 30) has a circular cross-section.

The exemplary elongate body distal portion 24 illustrated in FIG. 3 includes two lumens, a central lumen 32 through which diagnostic and therapeutic apparatus may be advanced and a steering wire lumen 34 in which the steering wire 22 is located. The central lumen 32 preferably terminates at the distal end 38 of the distal portion 24, thereby defining a distal end aperture through which diagnostic or therapeutic elements may exit the elongate body 14. However, the central lumen may also terminate in the side wall of the distal portion 24, thereby defining a side exit aperture. In the illustrated embodiment, the cross-sectional shape of the steering wire lumen 34 corresponds to that of the substantially flat steering wire distal portion 28. This prevents unwanted rotation of the steering wire 22. However, the steering wire lumen 34 may have other cross-sectional shapes, such as an elliptical shape, which will also prevent rotation of a non-circular steering wire or portion thereof.

As shown by way of example in FIG. 3, the steering wire 22 may be secured to an anchoring member 36 that is located within elongate body distal portion 24. The steering wire 22 may be secured to the anchoring member 36 by, for example, welding or adhesive. The exemplary anchoring member 36 is in the form of a cylinder. However, other shapes, such as an annular disk shape, could be used should they be required by a particular application. The anchoring member 36 provides a relatively long attachment surface, thereby decreasing the likelihood that the steering wire 22 will become disconnected from the elongate body distal portion 24. In addition, the anchoring member 36 may be formed from radiopaque material such as platinum or gold plated stainless steel. The radiopacity allows the distal portion of the elongate body to be observed by the physician using conventional fluoroscopic techniques. Other materials include rigid polymer and ceramic materials that are compounded with radiopaque material.

There are a number of advantages associated with the preferred embodiment illustrated in FIGS. 1-3. For example, when the distal portion 24 of the elongate body 14 is deflected from the orientation shown in FIG. 4a to the orientation shown in FIG. 4b, the steering wire will exert a force F along the elongate body distal portion. In conventional devices employing pull wires having a circular cross-section, the distal portion wall must be relatively thick in order to prevent the steering wire from tearing through the wall of the sheath or other elongate body. The wall in preferred embodiment illustrated in FIGS. 1-3 may be made thinner than conventional devices formed from the same material because the exemplary substantially flat (or otherwise non-circular) steering wire distal portion 28 distributes the force F over a greater surface area than does a steering wire having a circular cross-section.

The use of the present non-circular steering wire also prevents out of plane bending. In other words, when bending force is applied to the elongate body distal portion 24, it will bend about an axis that is both perpendicular to the longitudinal axis of the elongate body and parallel to the width dimension of the steering wire non-circular portion 28. The steering wire non-circular portion 28 also provides a larger surface area for attaching the steering wire to the exemplary anchoring member 36 (or other portion of the elongate body) than does a circular wire.

Figure 4:
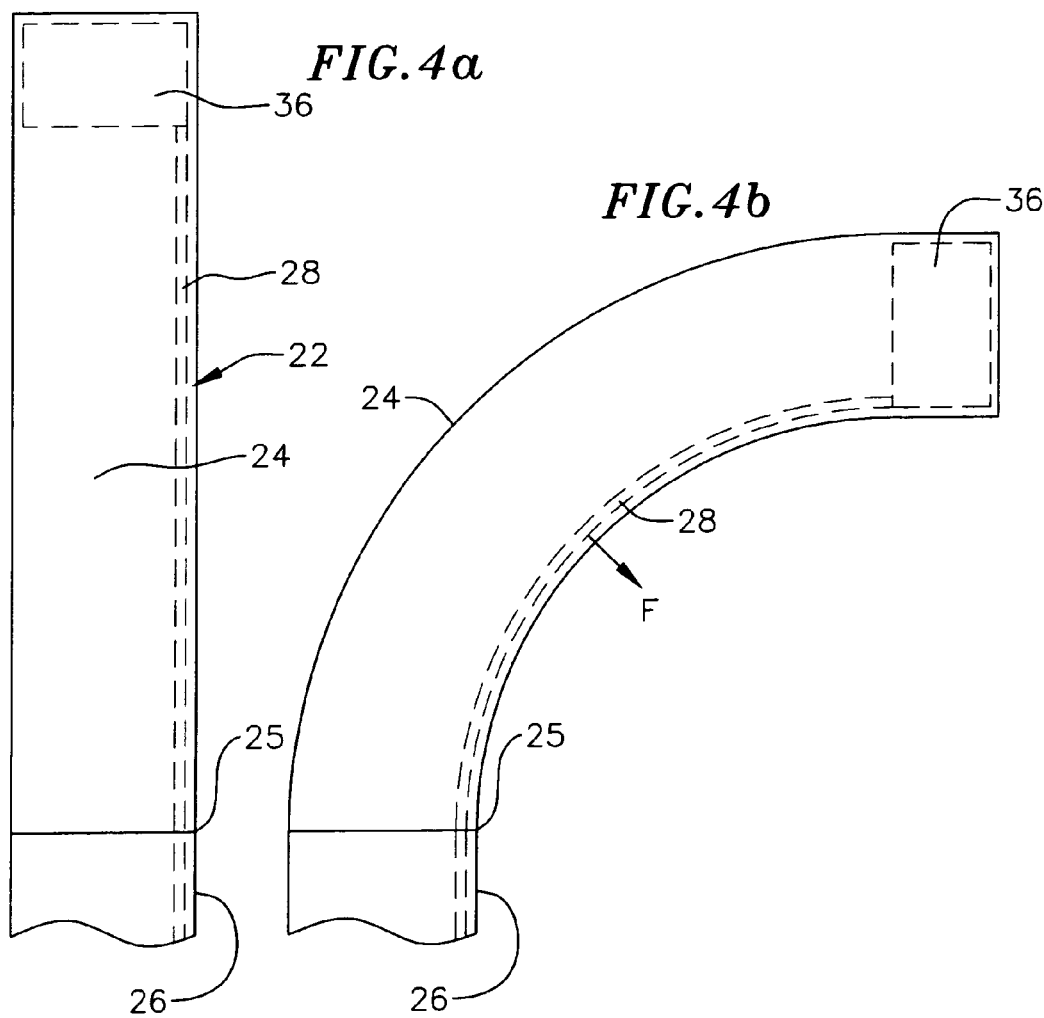
FIGS. 4a and 4b are side views of the elongate body distal portion illustrated in FIG. 3.

One utilization of the present invention is a steerable sheath that may be used in cardiac treatments such as percutaneous myocardial revascularization (PMR). In a preferred embodiment, the outer diameter of the elongate body 14 is about 0.118 inch and the diameter of the central lumen 32 is about 0.075 inch. The distal portion 24 of the elongate body is about 1.4 inches in length and should be flexible enough to bend approximately 135° (note that a 90° bend is shown in FIG. 4b), yet have sufficient memory to return to its original orientation when bending forces are removed. To provide the necessary flexibility, the distal portion 24 of the elongate body may be formed from a relatively flexible material through a dual lumen extrusion process. Preferred relatively flexible materials include, for example, fluoropolymers such as THV 200, a commercially available combination of tetrafluoroethylene, hexafluoropropylene and vinylidene fluoride, and Pellethane 80A. Radiopaque material, such as barrium, bismuth, and tungsten may be combined with the flexible material for visualization purposes.

In the exemplary steerable sheath that may be used in PMR and other cardiac care procedures, the anchoring member 36 is preferably about 0.100 inch in length and has a wall thickness of about 0.002 inch. The diameter of the circular proximal portion 30 of the steering wire 22 is about 0.009 inch, while the width of the non-circular portion 28 ranges from about 0.012 inch to about 0.017 inch and the thickness ranges from about 0.003 inch to about 0.005 inch. To accommodate the non-circular portion 28, the steering wire lumen 34 has a shape corresponding to that of the non-circular portion and cross-sectional dimensions which are about 0.001 inch to about 0.003 larger than those of the non-circular portion. The length of the steering wire non-circular portion 28 is preferably slightly less than that of the elongate body distal portion 24. As a result, only the circular proximal portion 30 of the steering wire 22 will pass through the circular steering wire lumen in the elongate body proximal portion 26 (discussed in Section III), even when the distal portion 24 is being bent. Alternatively, the non-circular portion 28 will extend the entire length of the elongate body distal portion 24 and the steering wire lumen in the elongate body proximal portion 26 will be modified accordingly.

Figure 5:
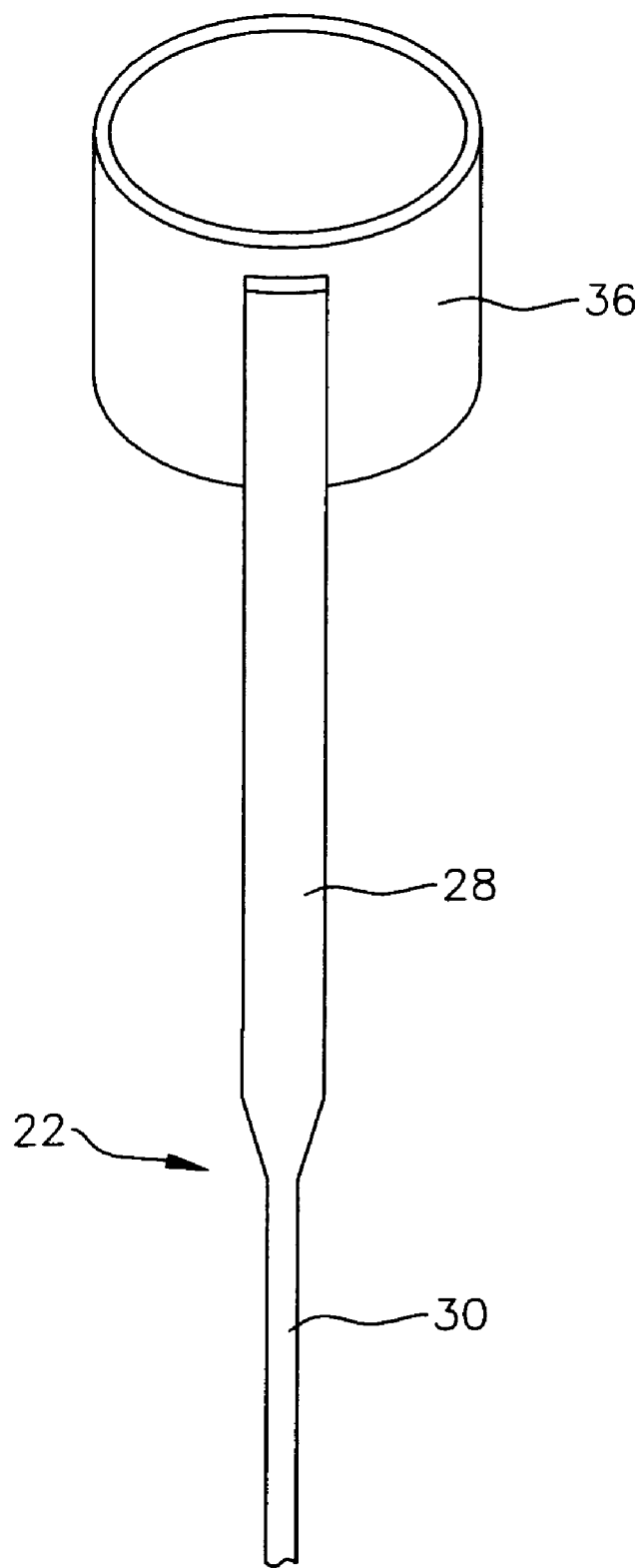
FIG. 5 is a perspective view of a steering wire and steering wire anchoring member assembly in accordance with a preferred embodiment of a present invention.

Turning to FIG. 5, the steering wire 22 may be secured to the anchoring member 36 prior to the insertion of both into the elongate body distal portion 24. The combined steering wire/anchoring member assembly may be inserted into the elongate body distal portion 24 as follows. The elongate body distal portion 24 is heated to its softening temperature. The proximal end of the steering wire 22 is then inserted into the steering wire lumen 34. The anchoring member 36 is moved toward the elongate body distal portion 24 until it reaches the distal end 38 of the distal portion. The anchoring member is then forced through the distal end 38 of the softened distal portion 24 to the position shown in FIG. 3.

Figure 6A:
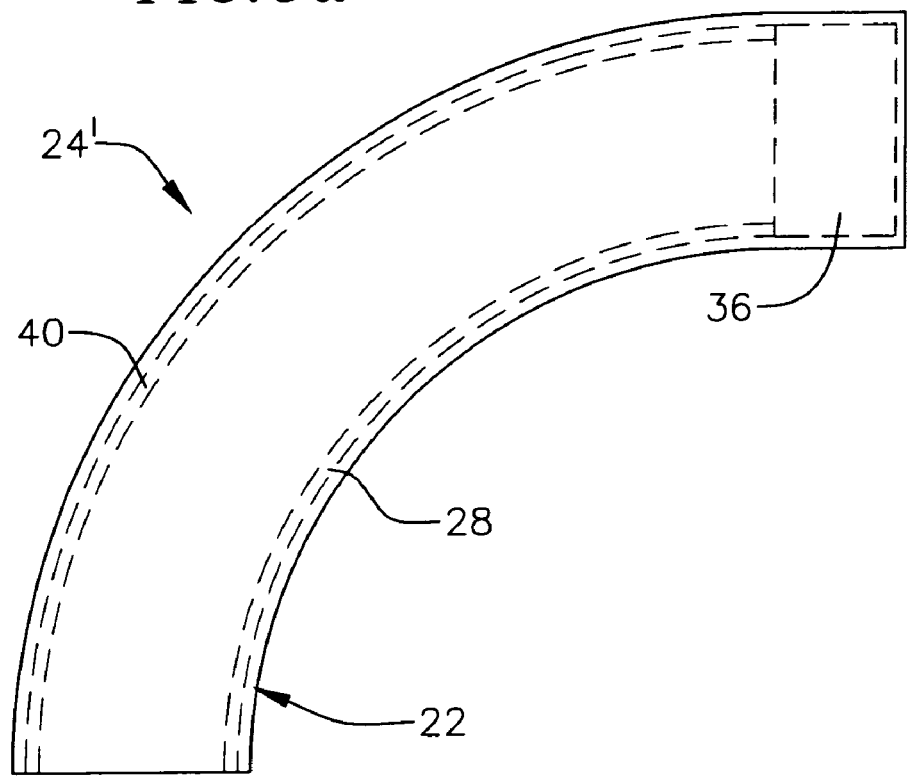
FIG. 6a is side view of an elongate body distal portion in accordance with another preferred embodiment of a present invention.
Figure 6B:
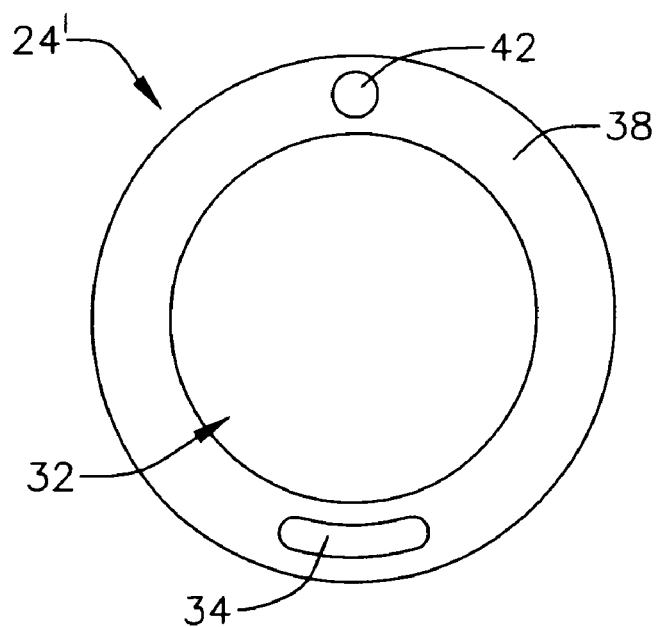
Figure 7A:
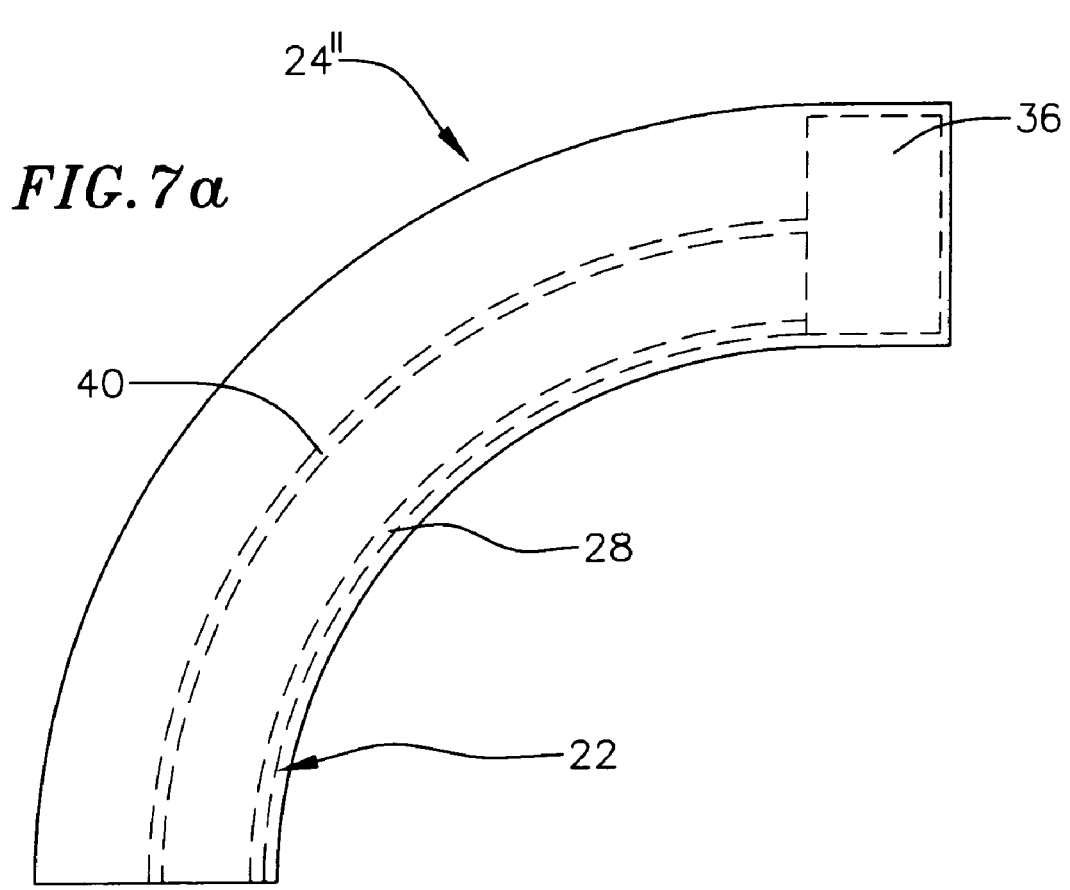
FIG. 7a is side view of an elongate body distal portion in accordance with still another preferred embodiment of a present invention.
Figure 7B:
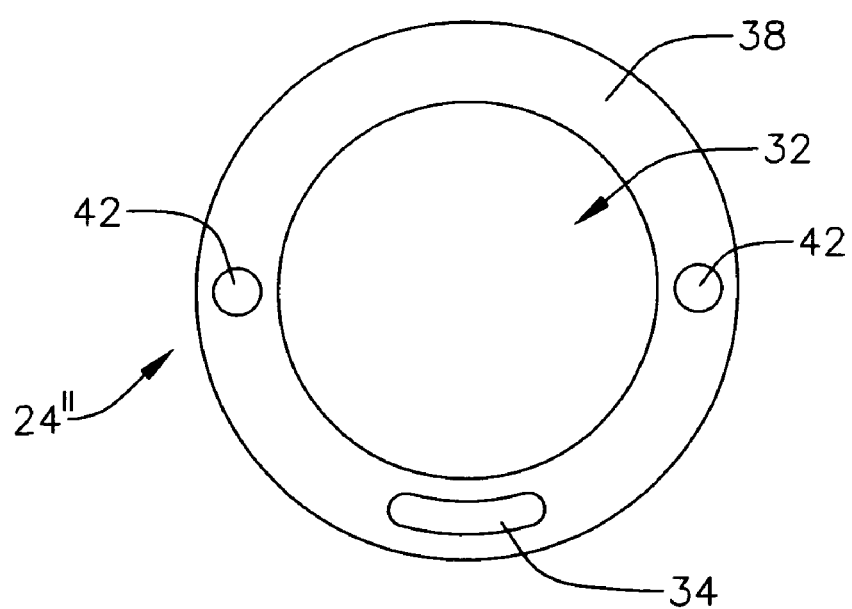

A stiffening member may be provided in order to prevent compression (or buckling) of the elongate body distal portion 24 during bending, which can sometimes happen in those instances where the distal portion is formed with very thin walls or from very flexible material. As shown by way of example in FIGS. 6a and 6b, an alternative elongate body distal portion 24' includes a stiffening member 40, which may be circular or non-circular in cross-section, located in a stiffening member lumen 42. The stiffening member lumen 42 is itself located on the side of the elongate body distal portion 24' opposite the steering wire 22 (and steering wire lumen 34). The stiffening member 40 is bonded or otherwise secured in place and is preferably formed from suitably rigid plastic or Nitinol material. Referring to FIGS. 7a and 7b, another alternative elongate body distal portion, identified by reference numeral 24", includes a pair of stiffening members 40 respectively located in a pair of stiffening member lumens 42. Although other configurations may be employed, the stiffening member lumens 42 in this embodiment are located 90° from the steering wire lumen 34 and 180° from one another.

Figure 8:
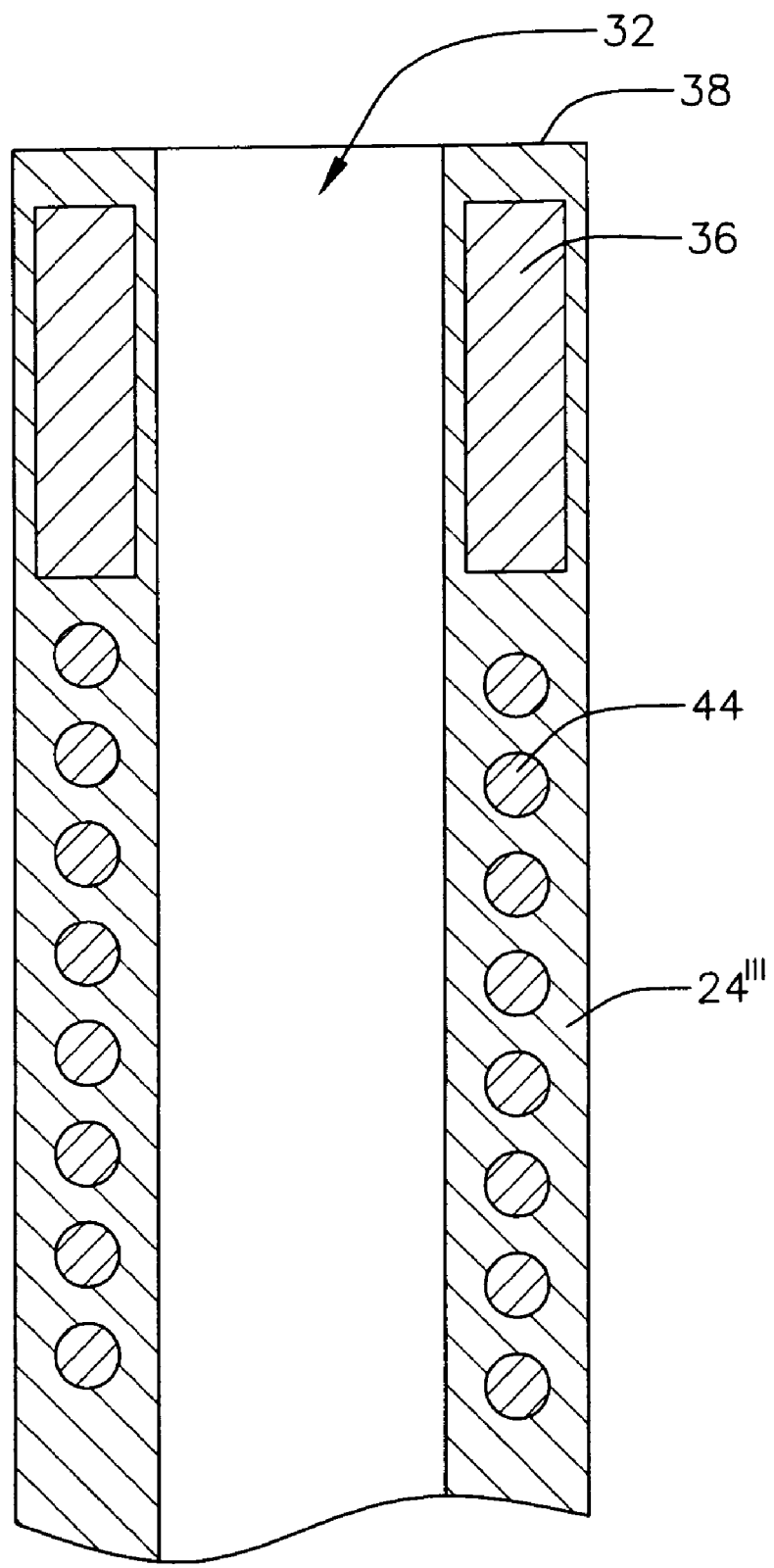
FIG. 8 is partial side section view of an elongate body distal portion in accordance with yet another preferred embodiment of a present invention.

A stiffening member may also be used to maintain the cross-sectional shape of the elongate body distal portion 24, which is circular in the illustrated embodiments. As illustrated for example in FIG. 8, an alternative elongate body distal portion 24''' includes a coil 44 embedded therein to help maintain the circular shape of the distal portion. Of course, the coil 44 and steering wire lumen 34 (not visible in FIG. 8) must be radially offset from one another within the distal portion 24'''.

III. Elongate Body Proximal Portion

Figure 9:
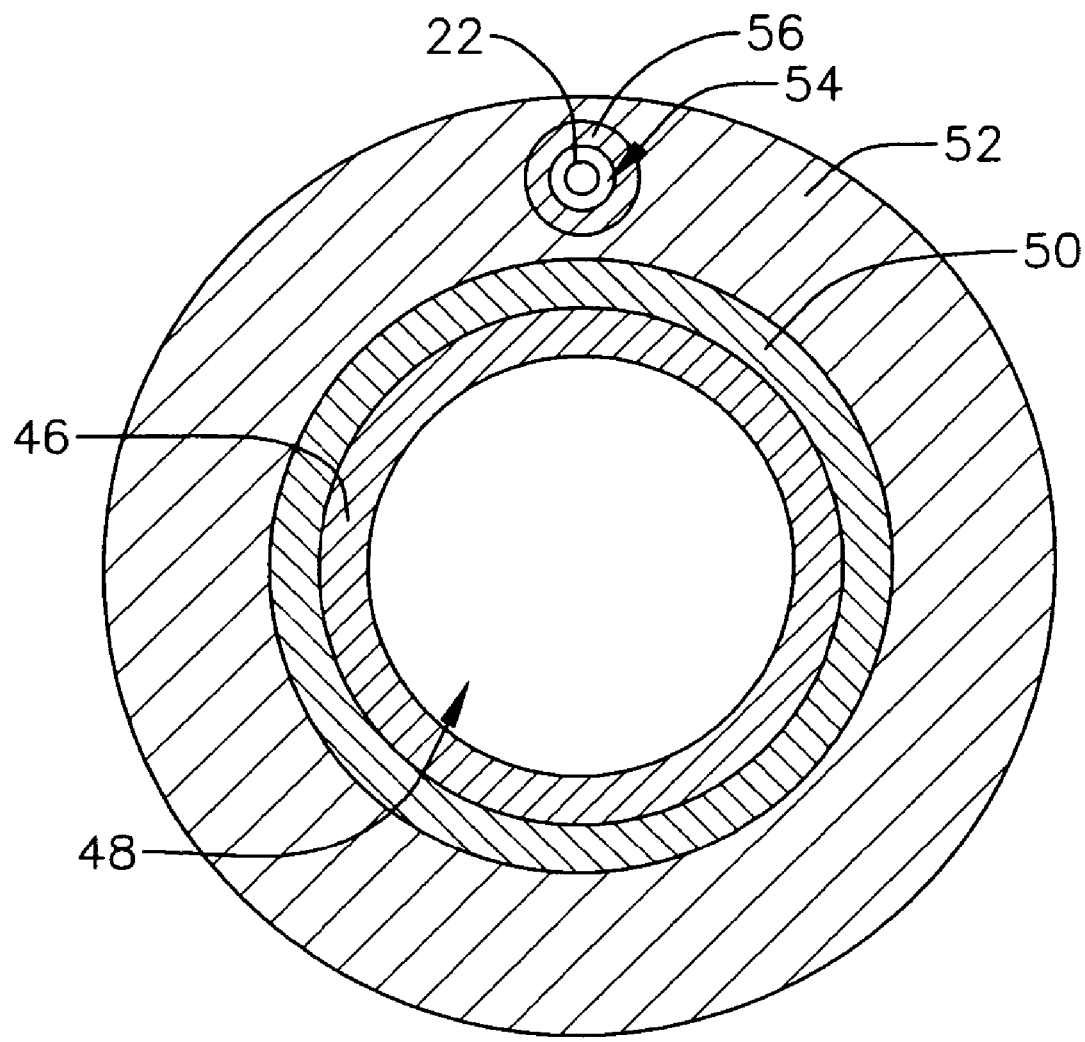
FIG. 9 is a section view taken along line 9-9 in FIG. 1.
Figure 10:
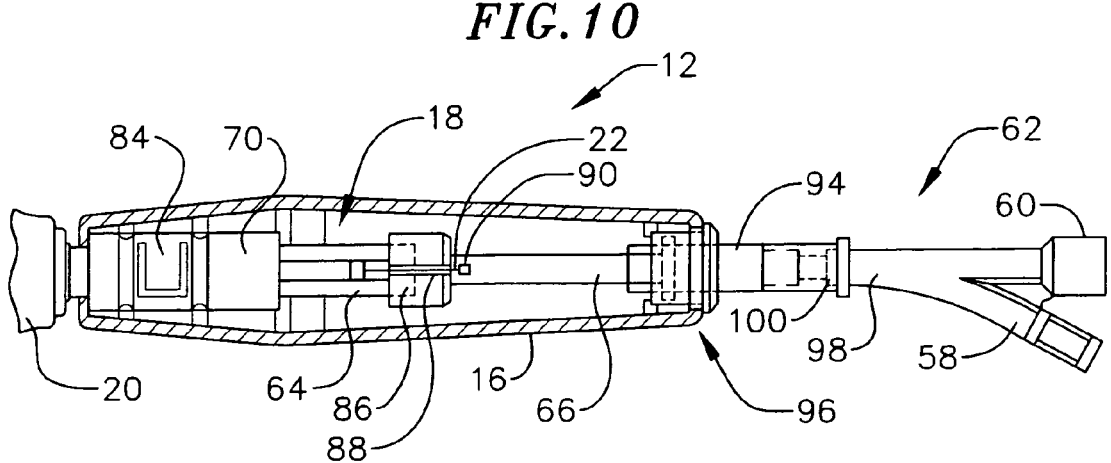
FIG. 10 is a partial cutaway view of the exemplary handle illustrated in FIG. 1.
Figure 11:
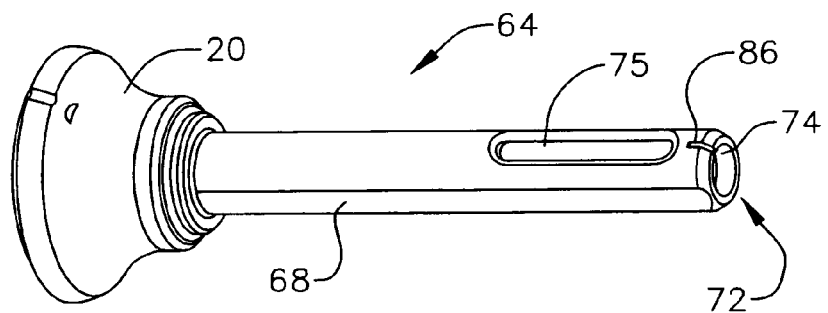
FIG. 11 is a perspective view of a portion of the exemplary handle illustrated in FIGS. 1 and 10.
Figure 12:
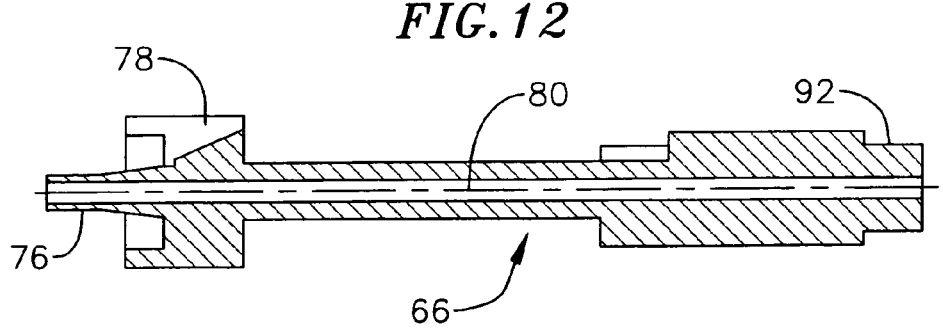
FIG. 12 is side partial section view of another portion of the exemplary handle illustrated in FIGS. 1 and 10.

As illustrated for example in FIG. 9, the exemplary elongate body proximal portion 26 includes an inner portion 46 through which a central lumen 48 extends, a reinforcing element 50, and an outer portion 52. The reinforcing element 50 increases the torque transmission properties of the proximal portion 26 and also increases its stiffness. The outer portion 52 includes a steering wire lumen 54 (note steering wire 22) which may be coated with a lubricious material 56 such as Teflon®. Although other material and structures may be used, the preferred reinforcing element is braided stainless steel having a braid pattern and pick number suitable for the intended application. Exemplary alternative reinforcing elements include double helix structures. Reinforcing elements, braided or not, may also be formed, for example, from Nylon® and other polymer materials.

The steering wire lumen 54 in the proximal portion 26 of the elongate body 14 is aligned with the steering wire lumen 34 in the distal portion 24. However, in contrast to the steering wire lumen 34, the steering wire lumen 54 is preferably circular in cross-section. In those embodiments where the length of the non-circular portion 28 of the steering wire 22 is less than the length of the elongate body distal portion 24, the steering wire lumen 54 in the proximal member may be circular in cross-section all the way to the distal end thereof. In other embodiments, where the steering wire non-circular portion 28 extends to the proximal end of the elongate body distal portion 24, the steering wire lumen 54 may be either non-circular in its entirety, or simply have a distal end that is chamfered into a funnel shape to accommodate the non-circular portion.

As noted in Section II, one implementation of the present invention is a steerable sheath that may be used in cardiac treatments such as PMR. Here, like the elongate body distal portion 24, the proximal portion 26 has an outer diameter of about 0.118 inch and the central lumen 48 (which is aligned with the central lumen 32 in the distal portion) has a diameter of 0.075 inch. The length of the proximal portion 26 in this implementation may be about 7 inches to about 70 inches. Also, a strain relief element (not shown) may be located over the proximal portion 26 near the thumb rest 20.

The proximal portion 26 may be formed by first extruding the inner portion 46 over a mandrel. The reinforcing element 50 is then placed over the inner portion 46. Next, the outer portion 52, including the steering wire lumen 54, is formed in a second extrusion. In those instances where the surface of the steering wire lumen 54 includes the coating of lubricious material 56, that coating is also formed during the second extrusion.

The distal and proximal portions 24 and 26 of the elongate body 14 are secured to one another at the joint 25. The joint may be formed in a variety of ways. For example, an adhesive or thermal butt bonding technique may be used. However, the preferred method is an overlapping thermal bond. Specifically, the distal and proximal portions 24 and 26 are arranged such that a small length of the distal portion overlaps the proximal portion (or vice versa). Heat is then applied to the overlapping region, which causes the overlapping portions to bond to one another.

The inner and outer portions 46 and 52 are both preferably formed from THV 200, which is fairly lubricious. Here, the lubricious coating 56 is not required. In other embodiments, the inner portion 46 is formed from a polyether block emide such as PEBAX®, which bonds well with an elongate body distal portion 24 that is formed from Pellethane, and the outer portion 52 is formed from a fluoropolymer such as THV 200. In still other embodiments, the inner portion 46 is formed from a fluoropolymer such as THV 200 and the outer portion 52 is formed from a polyether block emide such as PEBAX®. The lubricious coating 56 is especially useful here.

IV. Handle

An exemplary handle that may be used in conjunction with the elongate body 14 is the handle 12 illustrated in FIGS. 1 and 10-12. Similar handles are commonly found in steerable catheters manufactured by EP Technologies, Inc. under the trade name Polaris®, with one important exception. The piston 18 in the present handle 12 includes a lumen that connects the central lumen in the elongate body 14 to an input port 58 and a homeostasis valve 60. In the illustrated embodiment, the input port 58 and hemostasis valve 60 are part of a Y-adapter 62 that is capable of rotating 360°.

The exemplary piston 18 is a two-part assembly composed of a forward piston member 64 and a rear piston member 66. The forward piston member 64 includes a main body 68 which supports a portion of the thumb rest 20 at its distal end. The main body 68 extends into the handle body 16 through a piston supporting cylinder 70. The piston supporting cylinder 70 has o-rings at its longitudinal ends that center the main body 68. As shown by way of example in FIG. 11, a lumen 72 extends through the main body 68 and terminates at a frusto-conical surface 74. The proximal portion 26 of the elongate member 14 extends through the lumen 72 and outer surface of the proximal end of the elongate body is bonded to the conical surface 74. A key way 75, which mates with a protrusion on the inner surface of the handle, prevents the piston from rotating.

The exemplary rear piston member 66 includes a conical tip 76 that mates with the conical surface 74 (and distal end of the elongate body 14) and a cap 78 that fits over the forward member main body 68. The rear piston member 66 also includes a lumen 80 which feeds into the Y-adapter 62. To that end, the end 92 of the rear piston member 66 is inserted into the cylindrical portion 94 of the Y-adapter 62 and the two are sealed in a rear sealing assembly 96. The adapter stem 98 rotates relative to the cylindrical portion 94 and an o-ring 100 is provided to create a seal.

The level of friction between the piston 18 and handle body 16 may be controlled in part by a set screw 82 (FIG. 1) that imparts a force onto a tab 84 on the piston supporting cylinder 70.

Turning to the steering wire 22 and the manner in which it may be secured within the handle 12, the main body 68 of the exemplary forward piston member 66 includes a slot 86 at its distal end. The rear piston member cap 78 includes a corresponding slot 88. The steering wire 22 passes through the slots 86 and 88 and bends away from the central axis of the handle body 16. The distal end of the steering wire 22 is secured to an anchor 90 that is itself secured to the handle by a hollow nut and bolt assembly located on the half of the handle body 16 that is not shown in FIG. 10. Steering wire tension is set by rotating the bolt relative to the nut.

Although the present invention has been described in terms of the preferred embodiment above, numerous modifications and/or additions to the above-described preferred embodiments would be readily apparent to one skilled in the art. It is intended that the scope of the present invention extends to all such modifications and/or additions.

We claim:

1. An apparatus, comprising:

an elongate body proximal portion having a proximal end and a distal end and including a wall, defining an inner surface, an outer surface and a central lumen that extends from the proximal end to the distal end, and a steering wire lumen offset from the central lumen, located within the wall between the inner surface and the outer surface, extending from the proximal end to the distal end of the elongate body proximal portion and defining a circular cross-section;

an elongate body distal portion having a proximal end secured to the distal end of the elongate body proximal portion and including a wall, defining an inner surface, an outer surface and a central lumen extending from the proximal end of the elongate body proximal portion to a distal end aperture, and a steering wire lumen offset from the central lumen, located within the wall between the inner surface and the outer surface, extending from the proximal end to the distal end of the elongate body distal portion and defining a non-circular cross-section; and a steering wire having a proximal portion defining a circular cross-section and a distal portion defining a non-circular cross-section, the distal portion of the steering wire being operably connected to the distal portion of the elongate body at a location offset from the central lumen.

2. An apparatus as claimed in claim 1, further comprising:
a stiffening member associated with the distal portion of the elongate body.

3. An apparatus as claimed in claim 1, wherein the proximal portion of the elongate body is relatively stiff and the distal portion of the elongate body is relatively flexible.

4. An apparatus as claimed in claim 3, wherein the elongate body distal portion steering wire lumen defines a substantially flat cross-section.

5. An apparatus as claimed in claim 3, wherein the elongate body distal portion is longer than the steering wire distal portion.

6. An apparatus as claimed in claim 3, wherein the steering wire distal portion is secured to the elongate body distal portion adjacent to the distal end aperture.

7. An apparatus as claimed in claim 3, wherein the steering wire distal portion defines a proximal end, and the proximal end of the steering wire distal portion is located distal of the distal end of the elongate body proximal portion.

8. An apparatus as claimed in claim 3, wherein the steering wire distal portion defines a proximal end, and the proximal end of the steering wire distal portion extends to the distal end of the elongate body proximal portion.

9. An apparatus as claimed in claim 1, wherein the steering wire distal portion defines a substantially flat cross-section.

10. An apparatus as claimed in claim 9, wherein the steering wire lumen in the elongate body distal portion defines a substantially flat cross-section shape corresponding to the substantially flat cross-section of the steering wire distal portion.

11. An apparatus as claimed in claim 10, wherein the steering wire lumen in the elongate body distal portion defines cross-section dimensions that are about 0.001 inch to 0.003 inch greater than those of the steering wire distal portion.

12. An apparatus as claimed in claim 1, wherein the steering wire distal portion is secured to the elongate body distal portion adjacent to the distal end aperture.

13. An apparatus as claimed in claim 12, wherein the steering wire distal portion is secured to an anchoring member located within the elongate body distal portion.

14. An apparatus as claimed in claim 13, wherein the anchoring member is defines a substantially cylindrical shape.

15. An apparatus as claimed in claim 1, wherein the steering wire lumen is radially offset from the central lumen in the elongate body proximal portion.

16. An apparatus as claimed in claim 15, wherein the steering wire lumen is radially offset from the central lumen in the elongate body distal portion.

17. An apparatus as claimed in claim 1, wherein the steering wire is operably connected to the elongate body distal portion at a location within the wall between the inner surface and the outer surface.

18. An apparatus as claimed in claim 1, wherein the steering wire lumen in the elongate body proximal portion abuts the steering wire lumen in the elongate body distal portion.

19. An apparatus as claimed in claim 1, wherein the distal end aperture comprises an unobstructed distal end aperture.

* * * * *